US012751608B2

(12) United States Patent
Kok et al.

(10) Patent No.: US 12,751,608 B2
(45) Date of Patent: Oct. 6, 2026

(54) SYSTEM, METHOD AND COMPUTER PROGRAM FOR A SCIENTIFIC OR SURGICAL IMAGING SYSTEM, SCIENTIFIC OR SURGICAL IMAGING SYSTEM

(71) Applicant: Leica Instruments (Singapore) Pte. Ltd., Singapore (SG)

(72) Inventors: Alvin Kok, Singapore (SG); Jiahao Pan, Singapore (SG); Gao Yang, Singapore (SG); Zheng-Dong Zeng, Singapore (SG); Charles Zhang, Singapore (SG); Zhen Ye, Singapore (SG); Qingsong Zou, Singapore (SG); Gim Tong TEO, Singapore (SG)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 280 days.

(21) Appl. No.: 18/605,869

(22) Filed: Mar. 15, 2024

(65) Prior Publication Data

US 2024/0306904 A1 Sep. 19, 2024

(30) Foreign Application Priority Data

Mar. 15, 2023 (EP) .................................... 23161981

(51) Int. Cl.
*A61B 1/06* (2006.01)
*A61B 1/00* (2006.01)
(Continued)

(52) U.S. Cl.
CPC ........ *A61B 1/0655* (2022.02); *A61B 1/00165* (2013.01); *A61B 1/05* (2013.01); *A61B 3/0041* (2013.01)

(58) Field of Classification Search
CPC ..... A61B 1/0655; A61B 1/00165; A61B 1/05; A61B 1/00004; A61B 1/00009;
(Continued)

(56) References Cited

U.S. PATENT DOCUMENTS

| | | | | |
|---|---|---|---|---|
| 11,154,378 | B2 * | 10/2021 | Tesar | A61B 1/00193 |
| 2004/0227989 | A1 * | 11/2004 | Obrebski | G02B 21/20 359/388 |

(Continued)

FOREIGN PATENT DOCUMENTS

| | | | |
|---|---|---|---|
| EP | 3135185 | A1 | 3/2017 |
| EP | 4066729 | A1 | 10/2022 |

*Primary Examiner* — William R Alexander
(74) *Attorney, Agent, or Firm* — SPL Patent Attorneys PartG mbB; Yong Beom Hwang

(57) ABSTRACT

Examples relate to a system for a scientific or surgical imaging system, to a scientific or surgical imaging system comprising such a system, and to a corresponding method and computer program. The system comprises one or more processors and one or more storage devices. The system is configured to obtain information on one or more illumination parameters used by an illumination system, the illumination system being separate from the scientific or surgical optical imaging system, from the illumination system. The system is configured to determine at least one parameter for using an optical imaging sensor of an imaging device of the scientific or surgical optical imaging system based on the one or more illumination parameters.

15 Claims, 9 Drawing Sheets

(51) Int. Cl.
*A61B 1/05* (2006.01)
*A61B 3/00* (2006.01)

(58) Field of Classification Search
CPC ........... A61B 1/04; A61B 3/0041; A61B 3/13; A61B 3/14; A61B 3/0008; A61B 3/0016; A61B 3/0025; A61B 90/20; A61B 90/30; A61B 90/361; A61B 2090/306; A61B 2090/3612; A61B 34/10; A61B 90/37; G06N 20/00
USPC .......................................................... 351/206
See application file for complete search history.

(56) References Cited

U.S. PATENT DOCUMENTS

2009/0054879 A1* 2/2009 Berry ...................... A61F 9/008 606/5
2011/0261324 A1* 10/2011 Sander ................... A61B 3/132 351/221
2016/0074125 A1* 3/2016 Raymond ........... A61F 9/00825 606/107
2016/0250068 A1* 9/2016 Dewey ................ A61F 9/00825 606/4
2017/0020627 A1* 1/2017 Tesar ................... A61B 90/361
2021/0228284 A1* 7/2021 Voigt ..................... A61B 34/20
2022/0346650 A1* 11/2022 Novak ................... A61B 1/046
2023/0221539 A1* 7/2023 Kuebler ................. G02B 21/06 359/386
2024/0115345 A1* 4/2024 Park ......................... A61B 3/13

* cited by examiner

SYSTEM, METHOD AND COMPUTER PROGRAM FOR A SCIENTIFIC OR SURGICAL IMAGING SYSTEM, SCIENTIFIC OR SURGICAL IMAGING SYSTEM

TECHNICAL FIELD

Examples relate to a system for a scientific or surgical imaging system, to a scientific or surgical imaging system comprising such a system, and to a corresponding method and computer program.

BACKGROUND

A common pain point of surgeons operating in deep cavities is the lack of illumination and poor visibility of the surgical site. An endo-illumination system, such as an optical fiber or a chandelier used in retina surgeries, is inserted into the surgical cavity to provide visibility in such scenarios, e.g., during eye surgery. Adjustments to the wavelength of the light emitted by the respective illumination system(s) are performed during surgery to allow clearer visualization of the tissue features, stains, dyes, fluid, etc. In addition, the intensity of illumination over the surgical site varies during surgery, due to the movement of instruments, tissues and adjustments performed by the surgeon. For example, the intensity may be reduced to prevent retina damage and increased when visibility is poor.

Surgical cameras, i.e., cameras for use during surgical procedures, such as ophthalmological procedures, are generally fine-tuned to improve their performance. The settings enabling the improved performance are then often saved as "camera scene files", which are calibrated settings that are fixed (i.e., that do not change during surgery). In other words, the calibrated camera settings (such as exposure, color balance, contrast, shadows, highlights, brightness, saturation, vibrancy, sharpness, etc.) are fixed and not reacting to the real-time changes of the illumination system. Users may switch between these camera scene files or manually adjust settings during surgery when changing the illumination, e.g., the source of illumination, or consistently adjust the illumination settings during surgery if visualization is poor.

There may be a desire for an improved concept for providing illumination during surgery.

SUMMARY

This desire is addressed by the subject-matter of the independent claims.

Various examples of the present disclosure are based on the finding, that illumination systems used during surgery, and in particular endo-illuminators, are usually controlled by a computer system, by setting one or more illumination parameters, such as an illumination intensity parameter, an illumination angle parameter, and an illumination wavelength parameter. However, as such endo-illuminators are usually separate from the surgical imaging system (e.g., the surgical microscope), these illumination parameters are not controlled by the surgical imaging system. In the proposed concept, the illumination parameter(s) are provided, by the illumination system, to the surgical imaging system, and used by the surgical imaging system to adjust at least one parameter for using an optical imaging sensor, e.g., such as exposure, sensitivity, aperture, white balance etc. This enables an automatic adjustment of the at least one parameter for using the optical imaging sensor, and therefore an improved quality of a digital surgical view, without the hassle of manually selecting a scene file for the respective illumination setting being used. The same concept may be used in other scenarios as well, e.g., in scientific imaging, where specialized illumination systems are used to illuminate samples being observed using a scientific microscope.

Some aspects of the present disclosure relate to a system for a scientific or surgical optical imaging system. The system comprises one or more processors and one or more storage devices. The system is configured to obtain information on one or more illumination parameters used by an illumination system, the illumination system being separate from the scientific or surgical optical imaging system, from the illumination system. The system is configured to determine at least one parameter for using an optical imaging sensor of an imaging device of the scientific or surgical optical imaging system based on the one or more illumination parameters. This enables an automatic adjustment of the at least one parameter for using the optical imaging sensor, and therefore an improved quality of a digital surgical view, without the hassle of manually selecting a scene file for the respective illumination setting being used.

In the present context, the term "at least one parameter for using the optical imaging sensor" may be used both for a parameter being set at time of acquisition, such as an aperture parameter being used, an exposure parameter being used etc., as well as for a parameter being used for interpreting or processing the imaging sensor data. Accordingly, the system may be configured to determine at least one of an image processing parameter and an image acquisition parameter based on the one or more illumination parameters. Both types of parameters may benefit from the dynamic adjustment proposed herein.

For example, one or more of the following parameters may be adjusted based on the one or more illumination parameters. For example, the system may be configured to determine at least one of an exposure duration parameter, a sensitivity parameter, an aperture parameter, a brightness parameter, a shadow recovery parameter, a highlight recovery parameter, and at least one white balance parameter based on the one or more illumination parameters. For example, the latter parameter may be derived from, or constrained by, information on the wavelength spectrum being used by the illumination system. The former parameter(s) may be derived from, or constrained by, information on an illumination intensity and/or illumination angle of the illumination system. Accordingly, the one or more illumination parameters may comprise at least one of an illumination intensity parameter, an illumination angle parameter, and an illumination wavelength parameter. These parameters are particularly useful for setting various parameters related to exposure/brightness or color balance.

In general, imaging systems are capable of automatically setting parameters for using optical imaging sensors. The information on the one or more illumination parameters may be used as guideposts, to guide the automatic determination of the at least one parameter for using the optical imaging sensor, thus increasing the quality of the at least one determined parameter. Accordingly, the system may be configured to limit a search space for determining the at least one parameter for using the optical imaging sensor based on the one or more illumination parameters, and to determine the at least one parameter based on the limited search space. By limiting the search space, both the computational complexity for determining the at least one parameter may be reduced, and the quality of the determined at least one parameter may be increased, in particular in scenarios where multiple parameter values appear initially feasible.

For example, the system may be configured to limit a search space for determining at least one white balance parameter for using the optical imaging sensor based on at least one of an illumination intensity parameter and an illumination wavelength parameter included in the one or more illumination parameters. This may improve the quality of the white/color balance parameter, in particular in surgical settings, where often no neutral color is shown in the image frame. Additionally, or alternatively, the system may be configured to limit the search space for determining the at least one white balance parameter based on an expected composition of a sample being illuminated by the illumination system and being observed by the optical imaging sensor. In other words, starting from a known surgical scenario (such as retinal surgery or brain surgery, where the colors are mostly uniform across surgeries), the search space may be further constrained.

Similarly, the parameter(s) related to exposure may be determined within a limited search space. For example, the system may be configured to limit a search space for determining at least one of an exposure duration parameter, a sensitivity parameter, an aperture parameter, a brightness parameter, a shadow recovery parameter, and a highlight recovery parameter for using the optical imaging sensor based on at least one of an illumination intensity parameter and an illumination angle parameter included in the one or more illumination parameters.

To determine the parameter within the limited search space, a histogram that is based on the currently used parameters for using the optical imaging sensor may be used. For example, the system may be configured to determine at least one of the exposure duration parameter, the sensitivity parameter, the aperture parameter, the brightness parameter, the shadow recovery parameter, and the highlight recovery parameter based on the limited search space and based on a histogram of imaging sensor data of the optical imaging sensor. For example, if the histogram is inconclusive and presents two or more feasible options, the limited search space may indicate which of the two or more options to take.

In some examples, instead of a rule-based approach, machine-learning may be used to determine the at least one parameter. For example, the system may be configured to determine the at least one parameter for using the optical imaging sensor based on an output of a machine-learning model being trained to determine the at least one parameter, with the one or more illumination parameters and at least a histogram of imaging sensor data of the optical imaging sensor being used as input to the trained machine-learning model. This may both facilitate the decision-making and take into account prior actions taken by a user of the scientific or surgical imaging system.

In various examples, the system may be configured to adjust the machine-learning model, using supervised learning, during operation of the scientific or surgical imaging system using one or more sets of training data, each set of training data comprising the one or more illumination parameters, at least the histogram of the imaging sensor data, and at least one manually selected parameter for using the optical imaging sensor of an instance where a user has manually selected the at least one parameter. For example, over time, if the user decides to override the automatic determination of the at least one parameter for using the optical imaging sensor, the machine-learning model can be adjusted to the preferences of the user.

In the proposed concept, the illumination system, which may be an endo-illumination system, for example, is separate from the scientific or surgical imaging system. For example, the system may be configured to obtain the information on the one or more illumination parameters via at least one of a wired network connection, a wireless network connection, and an internet service from the illumination system. The connection being used may depend on the interoperability capabilities of the respective systems.

The present concept is applied to an optical imaging sensor of a scientific or surgical imaging system. Within the scientific or surgical imaging system, this optical imaging sensor may be used to generate a digital view of a surgical site or sample, based on the at least one parameter for using the optical imaging sensor. For example, the system may be configured to output a display signal to a display device of the scientific or surgical imaging system. The display signal may be based on the at least one parameter for using the optical imaging sensor and based on imaging sensor data of the optical imaging sensor. Thus, the user using the scientific or surgical imaging system via the display device may benefit from the automatic determination of the at least one parameter for using the optical imaging sensor.

Vis-à-vis the use of a scene file, the present concept is particularly useful in scenarios where the illumination of the sample changes of the time. For example, the system may be configured to update the at least one parameter for using the optical imaging sensor upon a change in the one or more illumination parameters. Thus, the at least one parameter for using the optical imaging sensor may be adapted to the changed one or more illumination parameters.

In some examples, the system may be configured to output a display signal to a display device of the scientific or surgical imaging system. The display signal may comprise a user interface for selecting a first mode for using the optical imaging sensor based on the at least one parameter being determined based on the one or more illumination parameters and for selecting a second mode for using the optical imaging sensor. The second mode may be based on at least one static parameter for using the at least on optical imaging sensor. In other words, the user may select either use a static scene file (e.g., as the user/surgeon is used to working with static scene files) or to use a mode where the at least one parameter is dynamically adjusted. This may provide each user with a suitable setting for using the scientific or surgical imaging system.

In the present disclosure, many examples are given with respect to ophthalmic microscopes. For example, the system may be a system for an ophthalmic microscope. The system may be configured to obtain the information on the one or more illumination parameters from an ophthalmic endo-illumination system. In this scenario, the proposed concept may be particularly beneficial, as the illumination often changes during eye surgery, and as the sample at hand (e.g., the retina) does not provide a color-neutral reference for white balancing.

Some aspects of the present disclosure relate to a scientific or surgical optical imaging system comprising an imaging device with an optical imaging sensor, and the above-referenced system.

Some aspects of the present disclosure relate to a corresponding method for a scientific or surgical optical imaging system. The method comprises obtaining, by the scientific or surgical optical imaging system, information on one or more illumination parameters used by an illumination system being separate from the scientific or surgical optical imaging system from the illumination system. The method comprises determining at least one parameter for using an optical imaging sensor of an imaging device of the scientific or surgical optical imaging system based on the one or more illumination parameters.

Another aspect of the present disclosure relates to computer program with a program code for performing the above method when the computer program is run on a processor.

SHORT DESCRIPTION OF THE FIGURES

Some examples of apparatuses and/or methods will be described in the following by way of example only, and with reference to the accompanying figures, in which:

FIG. 1*a* shows a schematic diagram of an example of a system for scientific or surgical imaging system;

FIG. 1*b* shows a schematic diagram of an example of a scientific or surgical imaging system that is coupled with an illumination system;

Figure 11A:
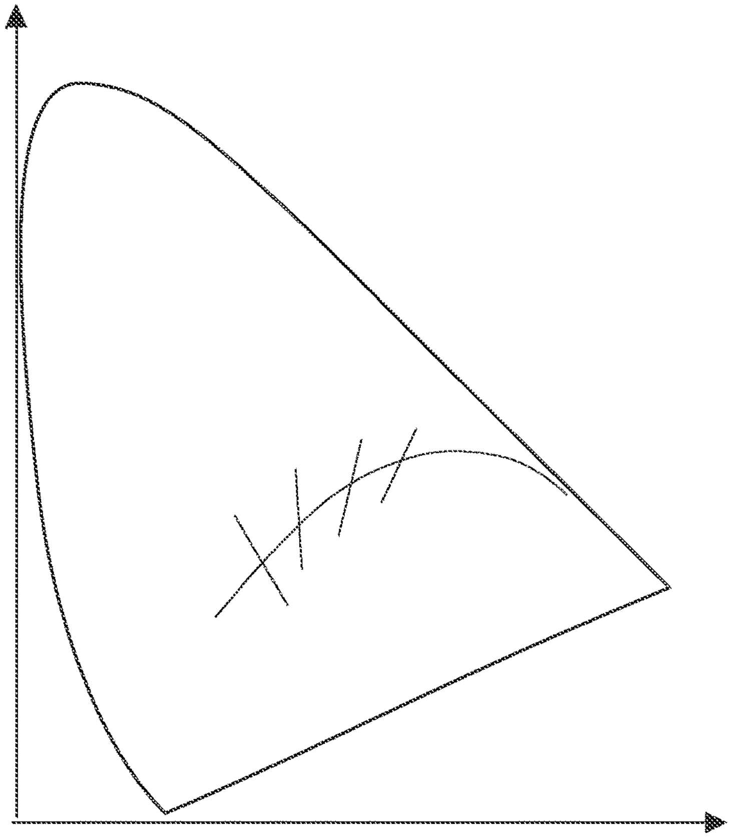
Figure 11B:
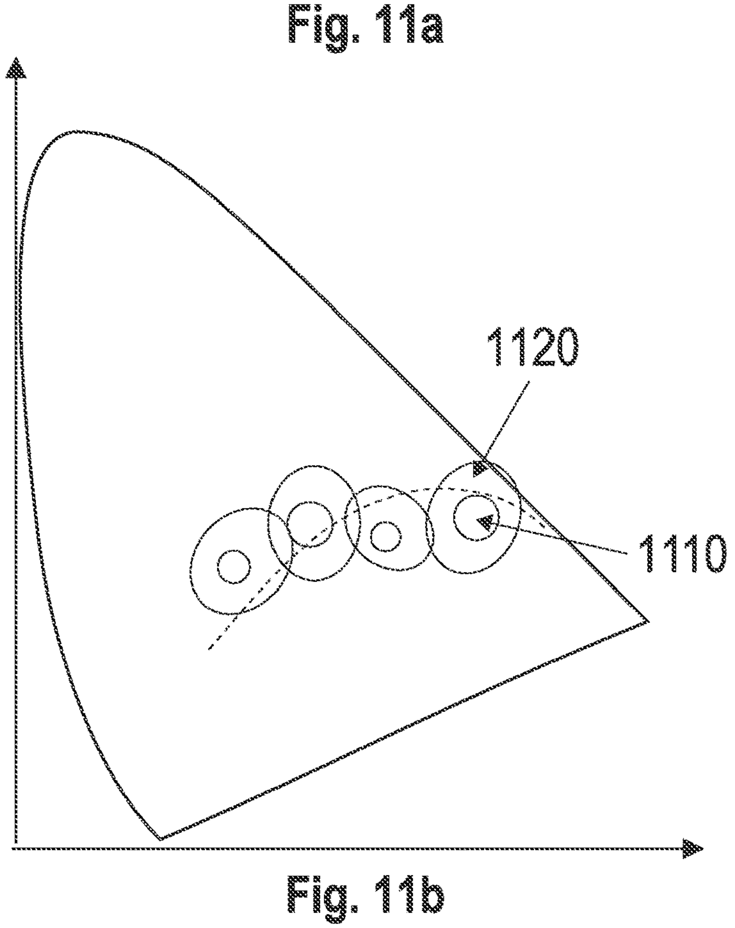
Figure 12:
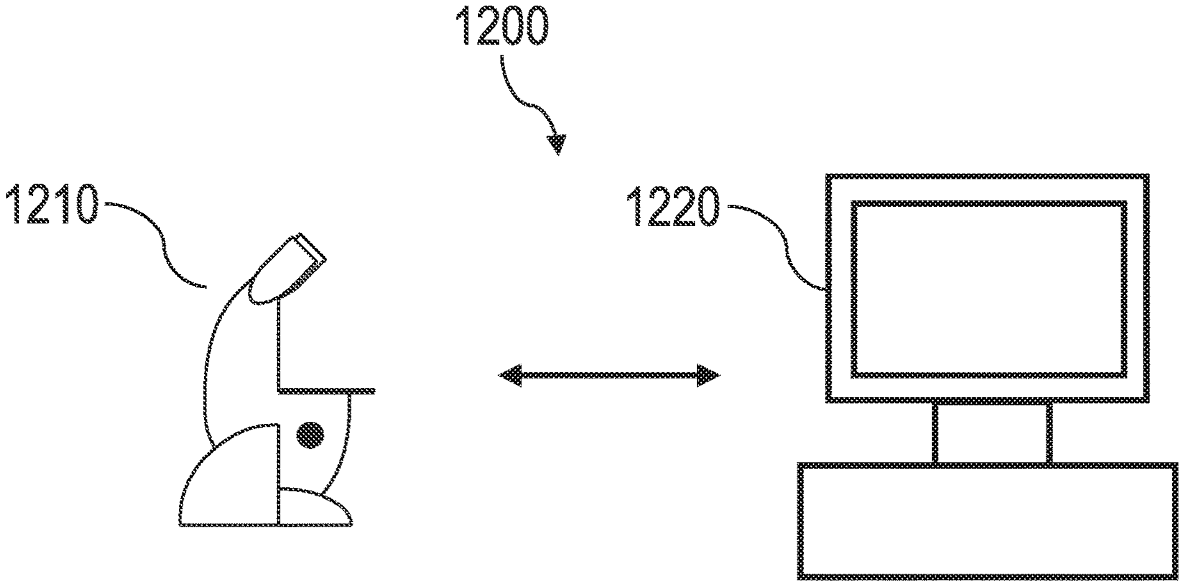

FIGS. 10*a* to 10*f* show an example of a determination of an exposure parameter;

FIGS. 11*a* and 11*b* show an example of dynamically determining a color balance; and FIG. 12 shows a schematic diagram of a system comprising a computer system and an optical imaging device.

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
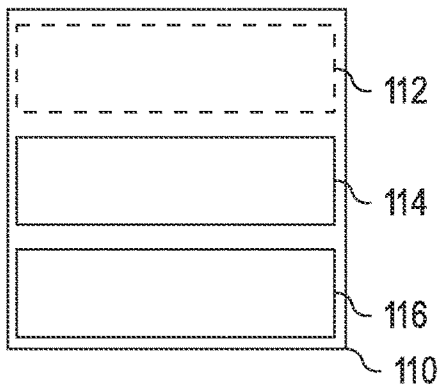
Figure 1B:
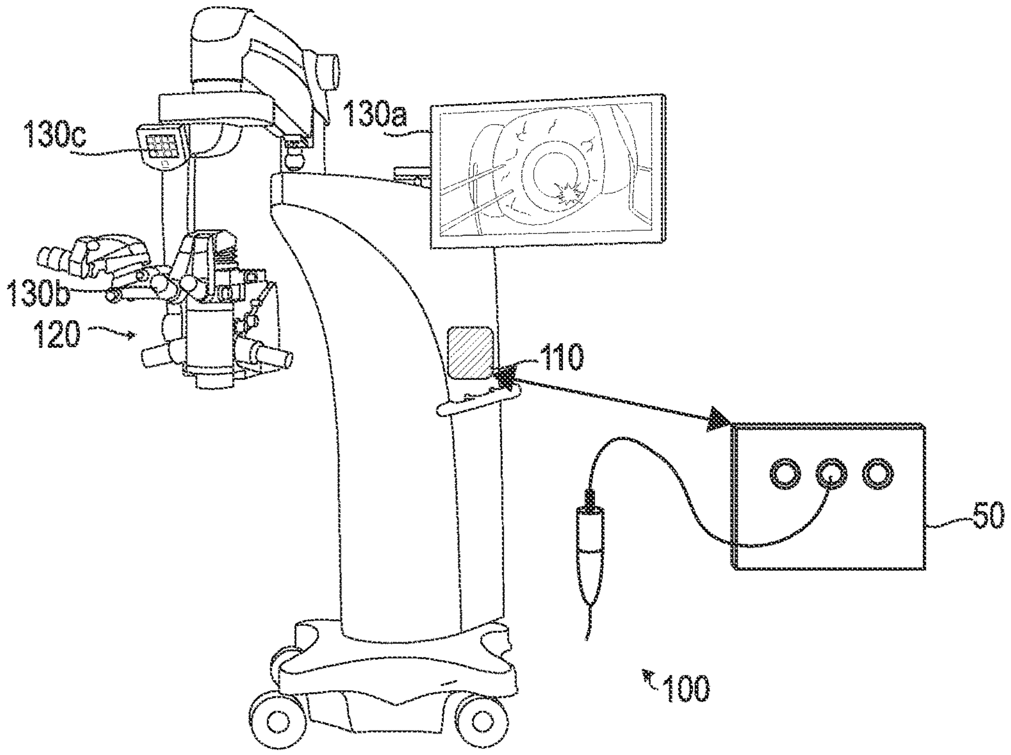

FIG. 1*a* shows a schematic diagram of an example of a system 110 for scientific or scientific or surgical imaging system 100 (shown in FIG. 1*b*). The system 110 is a component of the scientific or surgical imaging system 100 and may be used to control various aspects of the scientific or surgical imaging system 100. In particular, it may be used for acquisition and/or processing of imaging sensor data by an optical imaging sensor of an imaging device 120 of the scientific or surgical imaging system, through various means that will be introduced in more detail in the following. In addition, the system 110 may be configured to control additional aspects of the scientific or surgical imaging system, e.g., to provide a display signal for various displays of the scientific or surgical imaging system.

In general, the system 110 may be considered to be a computer system. The system 110 comprises one or more processors 114 and one or more storage devices 116. Optionally, the system 110 further comprises one or more interfaces 112. The one or more processors 114 are coupled to the one or more storage devices 116 and to the one or more interfaces 112. In general, the functionality of the system 110 may be provided by the one or more processors 114, in conjunction with the one or more interfaces 112 (for exchanging data/information with one or more other components of the scientific or surgical imaging system 100 and outside the scientific or surgical imaging system 100, such as an optical imaging sensor of the imaging device 120 and an illumination system 50 that is separate from the scientific or surgical imaging system), and with the one or more storage devices 116 (for storing information, such as machine-readable instructions of a computer program being executed by the one or more processors). In general, the functionality of the one or more processors 114 may be implemented by one or more processors 114 executing machine-readable instructions. Accordingly, any feature ascribed to the one or more processors 114 may be defined by one or more instructions of a plurality of machine-readable instructions. The system 110 may comprise the machine-readable instructions, e.g., within the one or more storage devices 116.

As outlined above, the system 110 is part of the scientific or surgical imaging system 100, which comprises various components in addition to the system 110. For example, the scientific or surgical imaging system 100 comprises the imaging device 120, and may comprise one or more additional components, such as one or more displays 130*a*-130*c*. FIG. 1*b* shows a schematic diagram of an example of such a scientific or surgical imaging system 100, and in particular of a surgical microscope system 100. In the following, the scientific or surgical imaging system 100 may also be referred to as surgical microscope system 100, which is a surgical imaging system 100 that comprises a (surgical) microscope as imaging device 120. However, the proposed concept is not limited to such embodiments. The scientific or surgical imaging system 100 may be based on various (single or multiple) imaging devices, such as one or more microscopes, one or more endoscopes, one or more exoscopes (also sometimes called an extracorporeal telescope). Exoscopes are camera-based imaging systems, and in particular camera-based 3D imaging systems, which are suitable for providing images of surgical sites with high magnification and a large depth of field. Compared to microscopes, which may be used via oculars, exoscopes are only used via display modalities, such as monitor or a head-mounted display. Accordingly, the scientific or surgical imaging system may alternatively be a surgical endoscope system, or a surgical exoscope system. Yet alternatively, the scientific or surgical imaging system may be scientific imaging system comprising a microscope, e.g., a laboratory microscope. However, the following illustrations assume that the surgical imaging device 120 is a surgical ophthalmic microscope, and that the scientific or surgical imaging system 100 is a surgical ophthalmic microscope system 100.

Accordingly, the scientific or surgical imaging system or surgical microscope system 100 may comprise an imaging device, such as a microscope 120. In general, a microscope, such as the microscope 120, is an optical instrument that is suitable for examining objects that are too small to be examined by the human eye (alone). For example, a microscope may provide an optical magnification of a sample. In the present concept, the optical magnification is (also) provided for an optical imaging sensor. The microscope 120 thus comprises an optical imaging sensor, which is coupled with the system 110. The microscope 120 may further comprise one or more optical magnification components that are used to magnify a view on the sample, such as an objective (i.e., lens). For example, the surgical imaging device or microscope 120 is often also called the "optics carrier" of the scientific or surgical imaging system.

There are a variety of different types of surgical imaging devices. If the surgical imaging device is used in the medical or biological fields, the object being viewed through the surgical imaging device may be a sample of organic tissue, e.g., arranged within a petri dish or present in a part of a body of a patient. In various examples presented here, the surgical imaging device 120 may be a microscope of a surgical microscope system, i.e., a microscope that is to be used during a surgical procedure, such as an ophthalmological procedure (i.e., eye surgery). Accordingly, the object being viewed through the surgical imaging device (that is shown in the field of view of the surgical imaging device) and shown in the digital view generated by based on the imaging sensor data provided by the (optional) optical imaging sensor, may be a sample of organic tissue of a patient, and may be in particular be the surgical site that the surgeon operates on during the surgical procedure, e.g., the eye. However, the proposed concept is also suitable for other types of surgery, such as neurosurgery or cardiac surgery.

FIG. 1*b* shows a schematic diagram of an example of a scientific or surgical imaging system 100, and in particular of a surgical ophthalmic microscope system 100, comprising the system 110 and a microscope 120. The surgical microscope system 100 shown in FIG. 1*b* comprises a number of optional components, such as a base unit (comprising the system 110) with a (rolling) stand, ocular displays 130*b* that are arranged at the microscope 120, an auxiliary display 130*a* that is arranged at the base unit, a small auxiliary display 130*c* that is arranged at the arm of the surgical ophthalmic microscope system 100, and the arm that holds the microscope 120 in place, and which is coupled to the base unit and to the microscope 120. In general, these optional and non-optional components may be coupled to the system 110 which may be configured to control and/or interact with the respective components. The scientific or surgical imaging system 100 (e.g., the system 110) is coupled with the external illumination system 50.

In the proposed concept, the system is used to determine at least one parameter for using an optical imaging sensor of an imaging device 120 of the scientific or surgical optical imaging system 100 based on information on one or more illumination parameters used by an illumination system 50 being separate from the scientific or surgical optical imaging system. In other words—the system uses knowledge about the parameters used by the external illumination system, to determine the at least one parameter for using the optical imaging sensor, and then uses the at least one parameter to obtain and/or process imaging sensor data from the optical imaging sensor.

The proposed concept starts by obtaining (e.g., receiving, reading out) the information on the one or more illumination parameters from the external illumination system. To give an example, as shown in connection with FIGS. 3 to 6, such an external illumination system may, for example, be an endo-illumination system. An endo-illuminator is a medical device that is used to provide illumination during minimally invasive surgery. The device usually comprises a light source and a fiberoptic cable that delivers light to the surgical site. Endo-illuminators are used in laparoscopic, thoracoscopic, and other types of minimally invasive surgery. In particular, the endo-illumination system being referred to in the present disclosure may be an endo-illumination system for use in retinal surgery, as shown in FIGS. 3 to 6, which are often inserted through the pars plana of the eye. Accordingly, the system 110 may be a system for an ophthalmic microscope. It may be configured to obtain the information on the one or more illumination parameters from an ophthalmic endo-illumination system 50. Such illumination systems are usually separate from the surgical ophthalmic microscope being used during the retinal surgery. In the proposed concept, one or more illumination parameters of the illumination systems are transmitted from the illumination system to the scientific or surgical microscope system (e.g., to the system 110 of the scientific or surgical microscope system). For example, the system may be configured to obtain the information on the one or more illumination parameters via at least one of a wired network connection, a wireless network connection, and an internet service from the illumination system. In particular, the system may be configured to obtain the information on the one or more illumination parameters according to standard ISO/IEEE 11073 SDC (International Standardization Organization/Institute of Electrical and Electronics Engineers standard 11073 "Service-oriented Device Connectivity"), which is a family of international standards for interoperable exchange of real-time information between medical devices and external systems in dynamic Internet Protocol (IP) networks.

To determine the at least one parameter for using the optical imaging sensor, two aspects of the illumination are of primary interest-how bright is the illumination applied to the sample, and what is the color spectrum of the illumination. The former is determined by two aspects—how bright is the light source (e.g., the lux intensity), and how large is the surface the illumination is applied to. Thus, the one or more illumination parameters may comprise at least one of an illumination intensity parameter (e.g., the lux intensity of the light source), and an illumination angle parameter, which determines the spread of the light beam, and thus also the surface onto which the light is protected. The color spectrum of the illumination can be obtained from an illumination wavelength parameter included in the one or more illumination parameters, i.e., a parameter indicating a color spectrum of the light provided by the illumination system.

Using the one or more illumination parameters, the system determines the at least one parameter for using the optical imaging sensor of the imaging device 120. In this context, the at least one parameter may both relate to a parameter being used during imaging sensor data acquisition by the optical imaging sensor, and to a parameter being used to process or interpret the imaging sensor data being provided by the optical imaging sensor. In other words, the system may be configured to determine at least one of an image processing parameter and an image acquisition parameter based on the one or more illumination parameters. To illustrate the difference—an image acquisition parameter may be used to control the optical imaging sensor during image acquisition, e.g., to control the optical imaging sensor to use a given exposure time per frame, to use a given sensor sensitivity ("ISO" value), or to use a given aperture. An image processing parameter may be used to interpret or process the imaging sensor data provided by the optical imaging sensor, e.g., to set the white point/color balance (in the present disclosure, color balance and white balance are used interchangeably) of a processed version of the imaging sensor data, to control a contrast adjustment of the processed version of the imaging sensor data, to control a brightness adjustment of the processed version of the imaging sensor data, to control shadow recovery being performed while generating the processed version of the imaging sensor data, and/or to control highlight recovery being performed while generating the processed version of the imaging sensor data. For example, the system may be configured to determine at least one of an exposure duration parameter, a sensitivity parameter, an aperture parameter (as image acquisition parameters), a brightness parameter, a shadow recovery parameter, a highlight recovery parameter (as image processing parameters), and at least one white balance parameter (can be image acquisition or image processing parameter) based on the one or more illumination parameters. Furthermore, the system may be configured to control the image acquisition of the optical imaging sensor (or imaging device, in the case of the aperture) using at least one image acquisition parameter. The system may be configured to obtain imaging sensor data from the optical imaging sensor, and to process or interpret the imaging sensor data based on the at least one image processing parameter to generate the processed imaging sensor data.

In the following, some examples are given on how the at least one parameter for using the optical imaging sensor can be determined. In general, an automatic determination of image acquisition and image processing parameters is mostly known in the context of digital imaging. For example, the imaging sensor data may be analyzed (e.g., by determining a histogram of the imaging sensor data), and the image acquisition and/or image processing parameters may be set based on the analysis of the imaging sensor data, e.g., to obtain a desired quality of the resulting processed imaging sensor data. In the proposed concept, this automatic determination process may be guided based on the one or more illumination parameters. To put it another way—with knowledge about the illumination, the search space for automatically determining the image acquisition and/or image processing parameter(s) can be limited. In other words, the system may be configured to limit a search space for determining the at least one parameter for using the optical imaging sensor based on the one or more illumination parameters, and to determine the at least one parameter based on the limited search space. Accordingly, the limited search space may then be used to guide the automated determination of the respective parameter for using the optical imaging sensor. The automated determination of the respective parameter, e.g., based on the histogram, is outside the scope of the present disclosure, and can be done according to industry practice, within in the limited search space.

In the following, two examples are given for determining such a limited search space, and for using the limited search space to determine the respective parameter for using the optical imaging sensor. The first example, which is illustrated in more detail in connection with FIGS. 10*a* to 10*f*, relates to the exposure setting being used. In the present context, the exposure setting may influence various parameters—with respect to image acquisition, the exposure setting may influence the exposure duration of the individual frames at the optical imaging sensor, the sensitivity of the optical imaging sensor, and an aperture of an iris placed between the optical imaging sensor and the sample being image. On the processing side, the exposure setting may influence the brightness adjustment, the contrast adjustment, the shadow recovery, and the highlight recovery being performed on the imaging sensor data. Accordingly, the system may be configured to limit a search space for determining the exposure setting, i.e., for determining at least one of an exposure duration parameter, a sensitivity parameter, an aperture parameter, a brightness parameter, a shadow recovery parameter, and a highlight recovery parameter for using the optical imaging sensor. This limited search space is determined based on the aforementioned brightness of the illumination applied to the sample, i.e., based on the illumination intensity and illumination angle. Accordingly, the system may be configured to determine the search space for determining the exposure setting based on at least one of an illumination intensity parameter and an illumination angle parameter included in the one or more illumination parameters. In the following, an example is given, with reference to FIGS. 10*a* to 10*f*, on how this can be achieved.

Figure 10A:
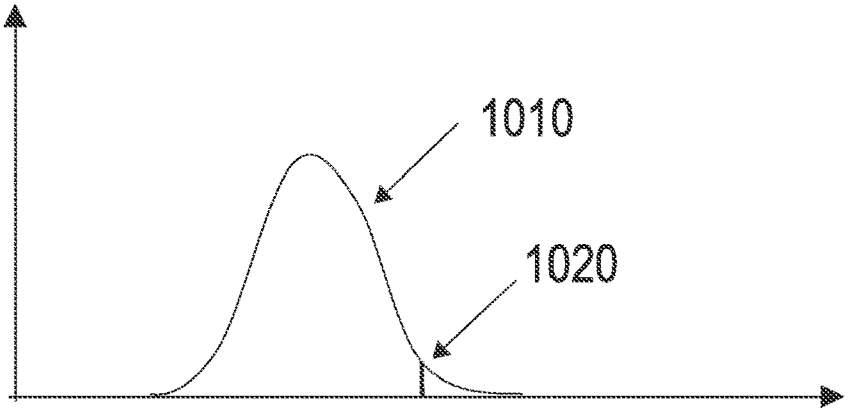
Figure 10B:
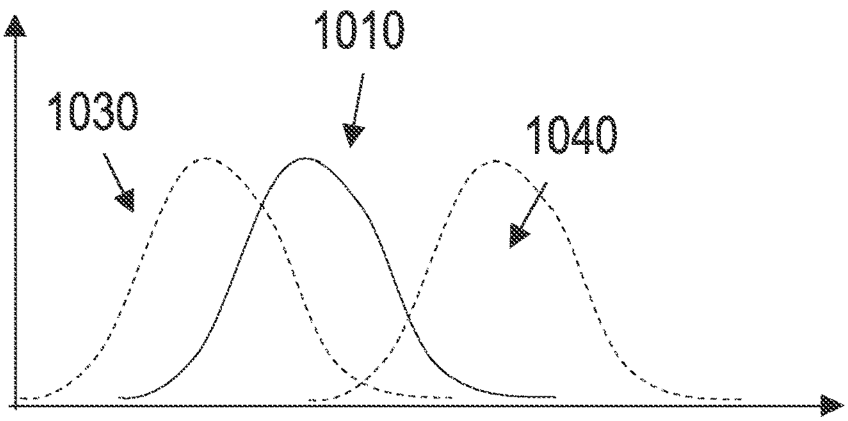
Figure 10C:
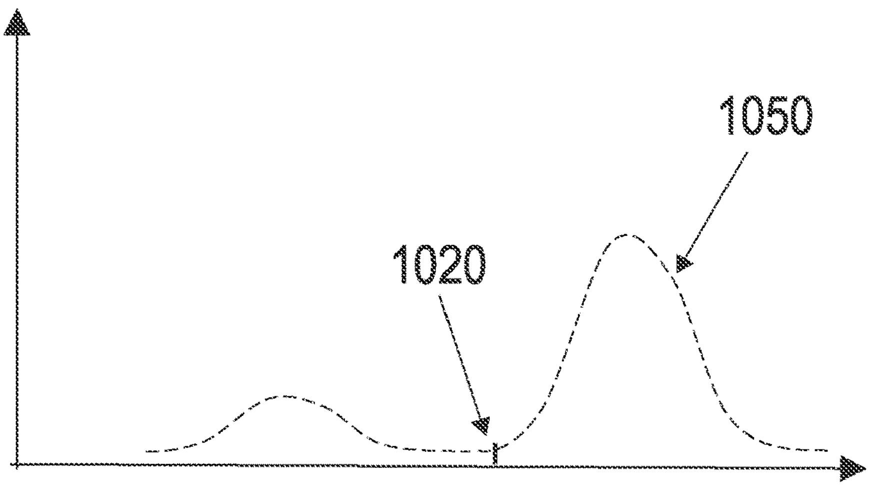
Figure 10D:
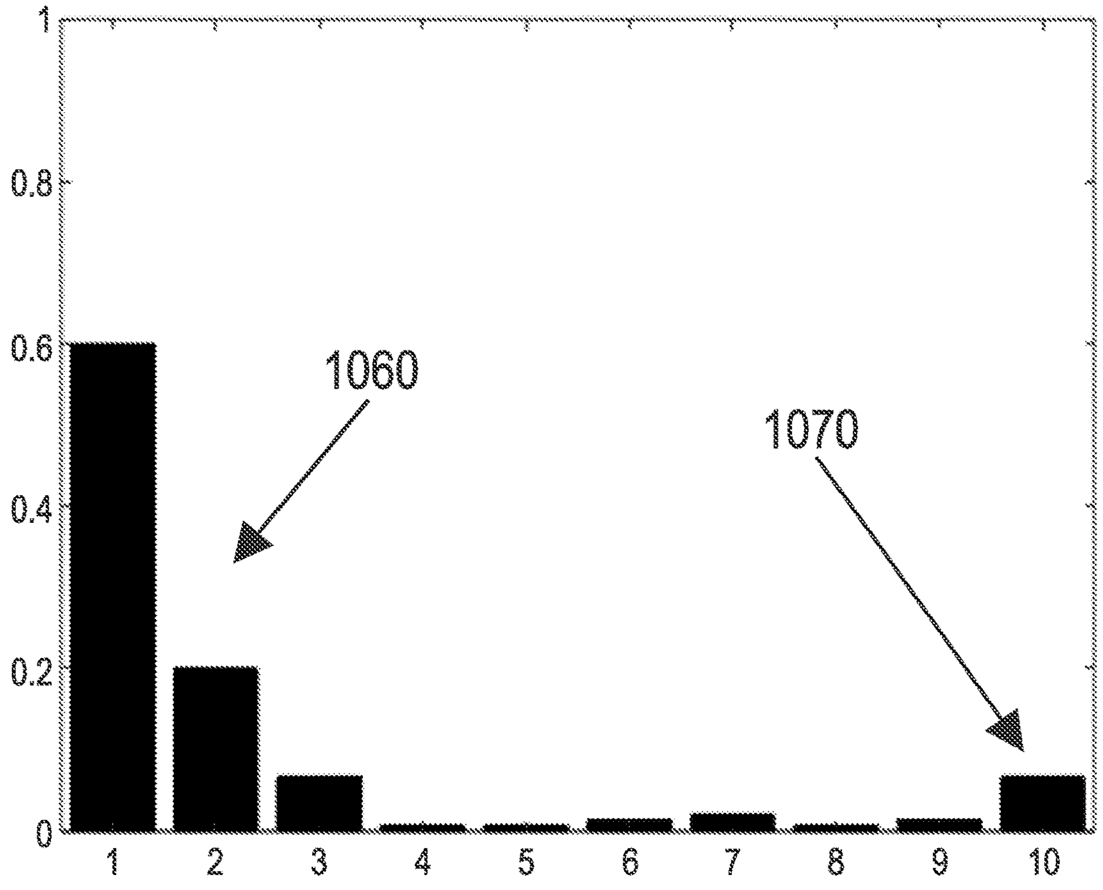
Figure 10E:
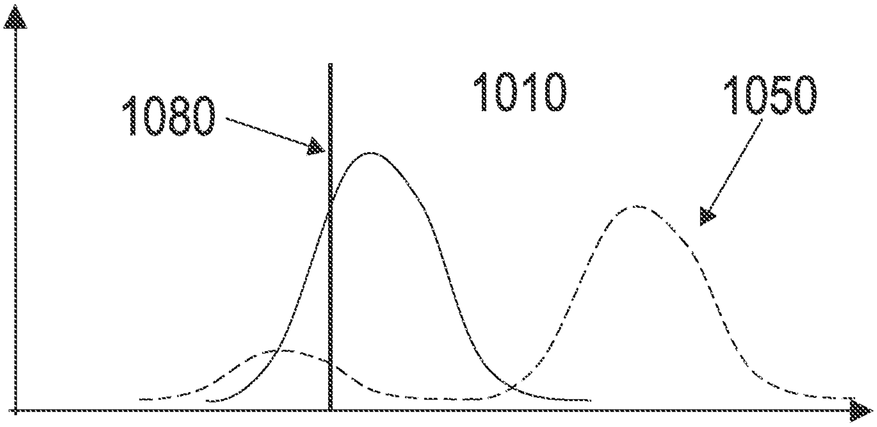
Figure 10F:
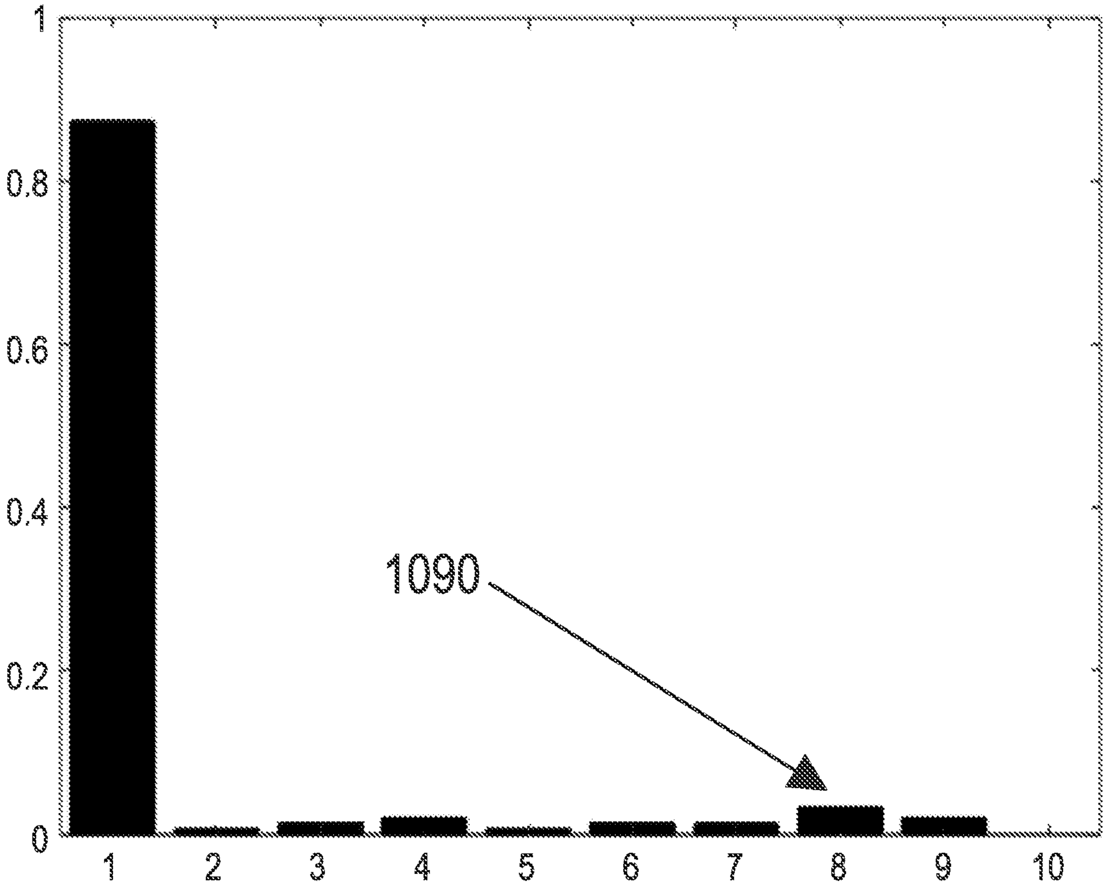

Using knowledge about the brightness of the sample, a likelihood function can be determined, for each illumination setting (e.g., for each combination of illumination intensity parameter and illumination angle parameter), with the illumination function indicating how likely a corresponding exposure setting is at the respective illumination setting. In FIG. 10*b*, three different likelihood functions 1030, 1010 and 1040 are shown for three different illumination settings. In the example of FIGS. 10*a* to 10*f*, the illumination setting 1010 is being used, which can be derived, by the system, from the one or more illumination parameters. In other words, the system may be configured to determine an illumination setting (e.g., combination of illumination intensity parameter and illumination angle parameter) being used, and to determine a likelihood function (e.g., use a predetermined likelihood function for the illumination setting) indicating how likely a corresponding exposure setting is at the respective illumination setting. In the example of FIGS. 10*a* to 10*f*, as shown in FIG. 10*a*, the initial exposure setting 1020 lies at the edge of the likelihood function of the illumination setting being used. To determine the "correct" (e.g., an improved) exposure setting, the histogram generated based on the initial exposure setting may be used (shown in FIG. 10*d*). In other words, the system may be configured to determine the exposure setting, e.g., at least one of the exposure duration parameter, the sensitivity parameter, the aperture parameter, the brightness parameter, the shadow recovery parameter, and the highlight recovery parameter based on the limited search space and based on a histogram of imaging sensor data of the optical imaging sensor. For example, the histogram may be used to determine another likelihood function indicating how likely a corresponding exposure setting is according to the histogram. As can be seen in FIG. 10*c*, the likelihood function 1050 that is derived from the histogram indicates that the exposure is either to be increased (to remedy underexposed portions indicated by the left portion 1060 of the histogram of FIG. 10*d*) or to be decreased (to remedy the overexposed portions indicated by the right portion 1070 of the histogram of FIG. 10*d*). Combining the two likelihood functions, as shown in FIG. 10*e*, shows that the exposure setting can be improved by reducing the exposure, as a maximum of a combination (e.g., multiplication) of the likelihood functions indicates the lowered exposure setting 1080. As a result, as shown in FIG. 10*f*, an even larger portion of the imaging sensor data is underexposed. However, the areas of interest within the imaging sensor data are now not saturated any more, enabling the user to see the area of interest more clearly.

With respect to color/white balance, a similar approach can be used. In this case, the system may be configured to limit a search space for determining at least one white balance parameter for using the optical imaging sensor based on at least one of an illumination intensity parameter and an illumination wavelength parameter included in the one or more illumination parameters. This is illustrated in FIGS. 11*a* and 11*b*. By knowing the image illumination wavelength parameter (and optionally the illumination intensity), the chromaticity spread of the light source (or light sources) can be determined and plotted onto a CIE (Commission Internationale de l'éclairage, international commission on illumination) 1931 chromaticity diagram.

There, they can limit the white balance search area. In FIG. 13*a*, the chromaticity spread of different light sources or light source settings is shown as the smaller circles 1110, with the ovals 1120 showing the white balance search area. The system may then limit the auto white balance search to some area in the vicinity of the chromaticity spread of the respective light source, e.g., with variable spread and likelihood values along different directions.

In both cases, the search space can be further limited if not only the respective illumination parameter(s) is/are known, but also the color properties of the sample, as the user perceives the reflection of light by the sample, which is, in turn, determined by the color and material composition of the sample. In other words, the system may be configured to limit the search space for determining the at least one white balance parameter based on an expected composition (e.g., color, shape, and reflectivity) of a sample being illuminated by the illumination system and being observed by the optical imaging sensor. For example, with respect to the first example, the likelihood functions of the different illumination settings may be determined for a specific expected composition of the sample, e.g., for a retina in the case of retinal surgery. Similarly, a likelihood function for determining the white balance from the chromaticity spread of the light sources may be determine for a specific expected composition of the sample.

In the previous examples, likelihood functions were primarily used to determine the respective parameter for using the optical imaging sensor. In some other implementations, the (explicit) likelihood functions may be replaced by a machine-learning model being trained to determine the respective parameter for using the optical imaging sensor. In other words, the system may be configured to determine the at least one parameter for using the optical imaging sensor based on an output of a machine-learning model being trained to determine the at least one parameter. At the input of the machine-learning model, the one or more illumination parameters and at least a histogram of imaging sensor data of the optical imaging sensor may be used.

In the following, a short introduction is given on machine-learning, and on the application of machine-learning in the present context. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g., words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g., sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e., each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g., a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied, and an unsupervised learning algorithm may be used to find structure in the input data (e.g., by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

In the proposed concept, supervised learning may be primarily used to train the machine-learning model. In particular in context of surgical microscopes, various pieces of data are recorded during surgery, e.g., for the purpose of replaying the surgery. Such recordings may now be used to train the machine-learning model. For example, the unprocessed version of imaging sensor data recorded during the surgery may be processed to generate a histogram of the imaging sensor data. Alternatively, the unprocessed version of the imaging sensor data may be used as input. In addition, the one or more illumination parameters may be recorded. The histogram or imaging sensor data and the one or more illumination parameters (which lead to the respective histogram) may be used as training inputs when training the machine-learning model. As desired training output, the parameter or parameter(s) for operating the optical imaging sensor selected by the respective surgeon may be used, which may be derived from the respective scene file selected by the surgeon. Thus, the machine-learning model may be trained, using supervised learning, on sets of training data, with each set of training data comprising the one or more illumination parameters, at least the histogram of the imaging sensor data (if not the imaging sensor data itself), and at least one manually selected parameter for using the optical imaging sensor. In some examples, the training may be performed by the system 110. However, preferably, the training may be done a priori by the manufacturer of the scientific or surgical imaging system.

However, the training may be continued, and thus the machine-learning model may be fine-tuned in situ by the system 110. For example, the system may be configured to adjust (i.e., fine-tune) the machine-learning model, using supervised learning, during operation of the scientific or surgical imaging system using one or more sets of training data. As above, each set of training data comprising the one or more illumination parameters, at least the histogram of the imaging sensor data (if not the imaging sensor data, or both), and at least one manually selected parameter for using the optical imaging sensor of an instance where a user has manually selected the at least one parameter. In other words, each time the user/surgeon decides to override the determined at least one parameter for using the optical imaging sensor, a set of training data may be generated, which may be used to fine-tune the machine-learning model.

A major advantage of the proposed concept vis-à-vis the selection of scene files is the automatism it provides-if the illumination is adjusted by the user, the one or more illumination parameters provided by the illumination system change. This may be used as a trigger to re-determine the at least one parameter for using the optical imaging sensor. In other words, the system may be configured to update the at least one parameter for using the optical imaging sensor upon a change in the one or more illumination parameters.

In the proposed concept, the at least one parameter for using the optical imaging sensor is determined such, that the resulting (processed) imaging sensor data provides an improved view on the sample. This improved view is provided as part of a digital view on the sample. This digital view (e.g., of the surgical site) is created and provided to a display of the surgical imaging system as part of a display signal. In other words, the system may be configured to output a display signal to a display device 130 of the scientific or surgical imaging system, with the display signal comprising the digital view. To generate the digital view, the system may be configured to generate the digital view based on the (processed) imaging sensor data, with (processed) imaging sensor data being generated based on the at least one parameter for using the optical imaging sensor. Accordingly, the display signal may be based on the at least one parameter for using the optical imaging sensor and based on imaging sensor data of the optical imaging sensor. The digital view may be viewed by the user, e.g., the surgeon, of the scientific surgical imaging system. For this purpose, the display signal may be provided to the display, e.g., an auxiliary display arranged at the base unit of the surgical microscope system, ocular displays integrated within the oculars of the surgical imaging device, or one or two displays of a head-mounted display. For example, the display signal may be a signal for driving (e.g., controlling) the respective display device. For example, the display signal may comprise video data and/or control instructions for driving the display. For example, the display signal may be provided via one of the one or more interfaces 112 of the system. Accordingly, the system 110 may comprise a video interface 112 that is suitable for providing the display signal to the display 130 of the microscope system 100.

Figure 8:
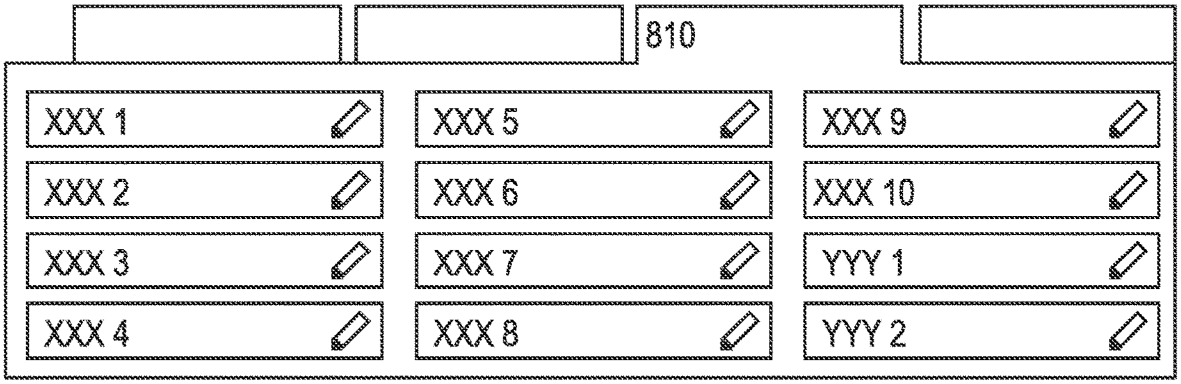
FIG. 8 shows a schematic diagram of a user interface allowing a user to select a scene file or a dynamic scene file.

In addition to the digital view, the displays may also be used to present a user interface to a user of the scientific or surgical imaging system. In this case, the display signal may comprise a user interface for selecting different modes for using the optical imaging sensor. For example, user interface may be shown for selecting a first mode for using the optical imaging sensor and for selecting a second mode for using the optical imaging sensor. For example, one of the modes (e.g., the first mode) may be based on the proposed concept, i.e., based on the at least one parameter being determined based on the one or more illumination parameters. The other mode (e.g., the second mode) may be based on at least one static parameter for using the at least on optical imaging sensor. In other words, the first mode may be a dynamic mode, and the second mode may be based on a static scene file. An example of such a user interface is shown in FIG. 8.

In the proposed scientific or surgical imaging system, the optical imaging sensor is used to provide the aforementioned imaging sensor data. Accordingly, the optical imaging sensor, which may be part of the scientific or surgical imaging device 120 (e.g., of the microscope) may be configured to generate the imaging sensor data. For example, the optical imaging sensor of the surgical imaging device 120 may comprise or be an APS (Active Pixel Sensor)—or a CCD (Charge-Coupled-Device)-based imaging sensor. For example, in APS-based imaging sensors, light is recorded at each pixel using a photodetector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensors by a circuitry of the imaging sensors to perform the imaging. The system 110 may be configured to obtain (i.e., receive or read out) the imaging sensor data from the optical imaging sensor. The imaging sensor data may be obtained by receiving the imaging sensor data from the optical imaging sensor (e.g., via the interface 112), by reading the imaging sensor data out from a memory of the optical imaging sensor (e.g., via the interface 112), or by reading the imaging sensor data from a storage device 116 of the system 110, e.g., after the imaging sensor data has been written to the storage device 116 by the optical imaging sensor or by another system or processor.

The one or more interfaces 112 of the system 110 may correspond to one or more inputs and/or outputs for receiving and/or transmitting information, which may be in digital (bit) values according to a specified code, within a module, between modules or between modules of different entities. For example, the one or more interfaces 112 may comprise interface circuitry configured to receive and/or transmit information. The one or more processors 114 of the system 110 may be implemented using one or more processing units, one or more processing devices, any means for processing, such as a processor, a computer or a programmable hardware component being operable with accordingly adapted software. In other words, the described function of the one or more processors 114 may as well be implemented in software, which is then executed on one or more programmable hardware components. Such hardware components may comprise a general-purpose processor, a Digital Signal Processor (DSP), a micro-controller, etc. The one or more storage devices 116 of the system 110 may comprise at least one element of the group of a computer readable storage medium, such as a magnetic or optical storage medium, e.g., a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the system and scientific or surgical imaging system are mentioned in connection with the proposed concept, or one or more examples described above or below (e.g., FIGS. 2 to 12). The system and/or scientific or surgical imaging system may comprise one or more additional optional features corresponding to one or more aspects of the proposed concept, or one or more examples described above or below.

Figure 2:
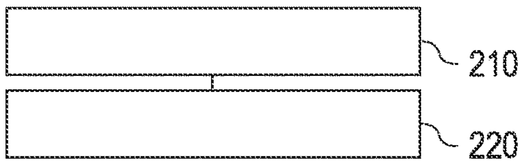
FIG. 2 shows a flow chart of an example of a method for a scientific or surgical imaging system.

FIG. 2 shows a flow chart of an example of a method for a scientific or surgical imaging system. For example, the method may be performed by the scientific or surgical imaging system 100 shown in FIG. 1*b*, and in particular by the system 110 shown in FIGS. 1*a* and 1*b*. The method comprises obtaining 210, by the scientific or surgical optical imaging system, information on one or more illumination parameters used by an illumination system being separate from the scientific or surgical optical imaging system from the illumination system. The method comprises determining 220 at least one parameter for using an optical imaging sensor of an imaging device of the scientific or surgical optical imaging system based on the one or more illumination parameters. Features discussed in connection with the scientific or surgical imaging system of FIGS. 1*a* to 1*b* and 3 to 12 may likewise be included in the method of FIG. 2.

More details and aspects of the method are mentioned in connection with the proposed concept, or one or more examples described above or below (e.g., FIG. 1*a* to 1*b*, 3 to 12). The method may comprise one or more additional optional features corresponding to one or more aspects of the proposed concept, or one or more examples described above or below.

Various examples of the present disclosure relate to a concept (e.g., a method) for dynamic calibration of camera settings based on real-time illumination information ("Dynamic Camera"). The proposed concept relates to an approach for automatic calibration of the surgical image based on inputs from an illumination system. A common pain point of surgeons operating in deep cavities is the lack of illumination and poor visibility of the surgical site. In ophthalmology, the lack of visibility of the retina workflow is a frustration among surgeons.

Current endo-illumination systems for ophthalmology provide an optical fiber or chandelier which can be inserted into the posterior cavity of the eye, surgeons are able to adjust the lux intensity and wavelength throughout the procedure depending on the current workflow (e.g., lowering lighting during liquid-air exchange to reduce reflections, changing wavelengths to better visualize a stained membrane).

Figure 3:
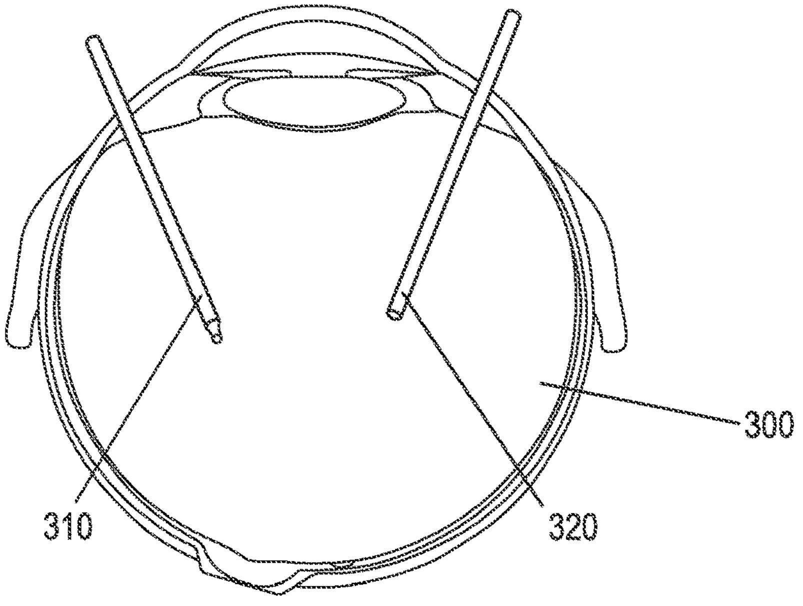
FIGS. 3, 4 and 5 show schematic diagrams of endo-illumination systems for retinal surgery.
Figure 4:
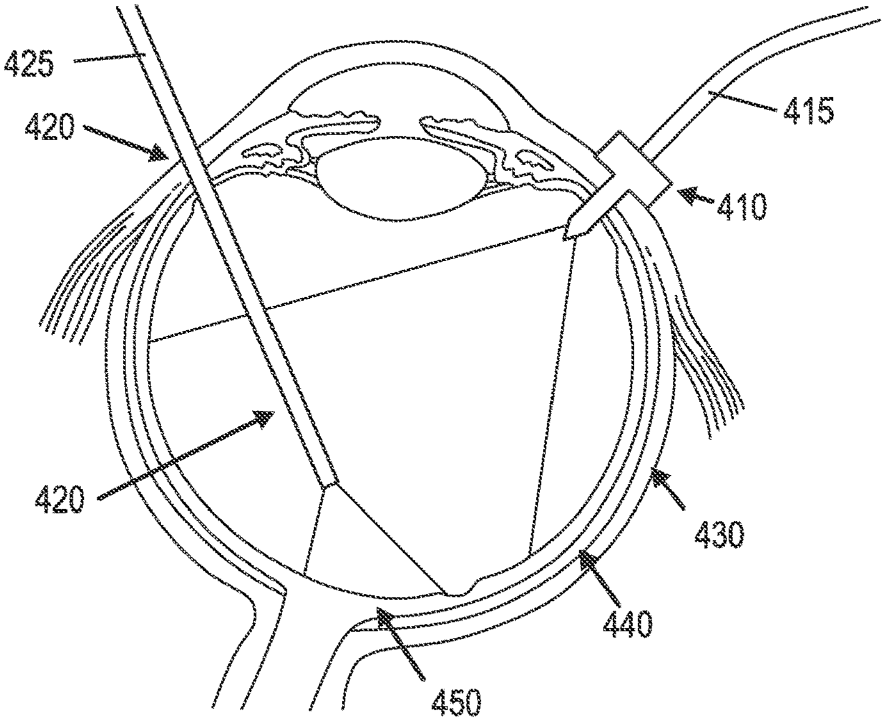
Figure 5:
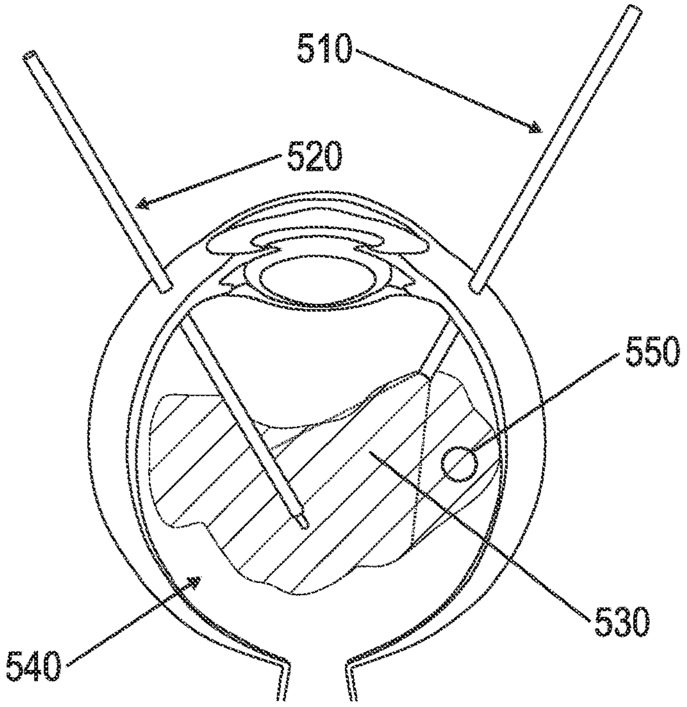

FIGS. 3, 4 and 5 show schematic diagrams of endo-illumination systems for retinal surgery. In FIG. 3, an eye 300 is shown, with an endo-illuminator 310 as light source and a vitreous cutter 320. In FIG. 4, an eye is shown with a chandelier endoilluminator 410 (and corresponding connection 415 to a Xenon light source, a second endoilluminator implemented by a rigid optical fiber 420 entering through the pars plana (and corresponding connection 425 to a Xenon light source). FIG. 4 further shows the sclera 430, the choroid 440 and the retina 450 of the eye. In FIG. 5, a light source 510 (with resulting light beam 530) and a vitrector 520 are shown entering the vitreous of the eye. FIG. 5 further shows the retina 540, and bleeding 550.

Figure 6:
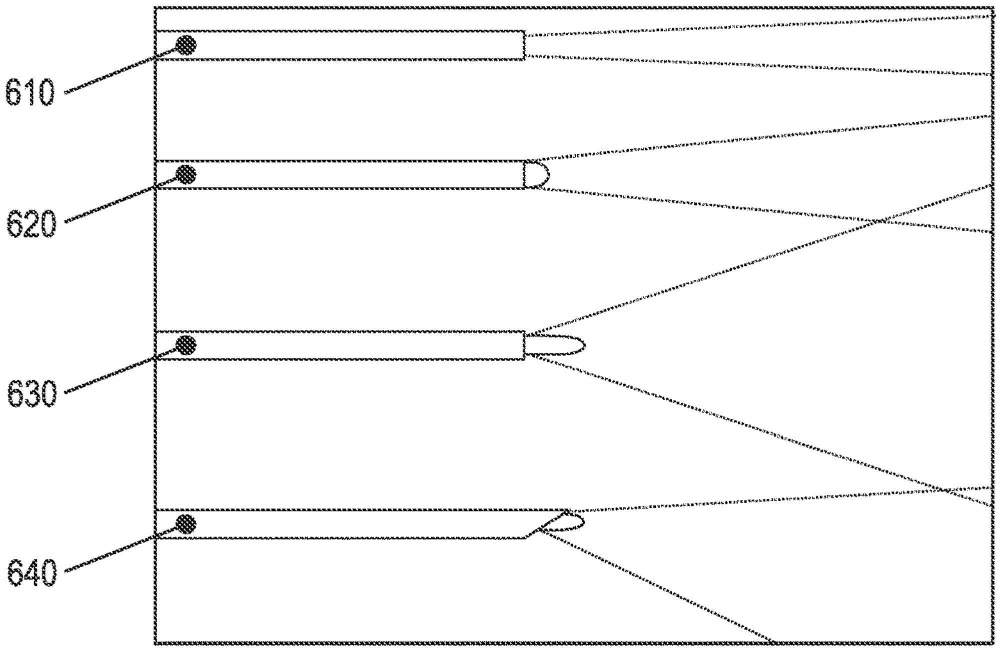
FIG. 6 shows schematic drawings of examples of different types of light beams generated by endo-illuminators.
Figure 7:
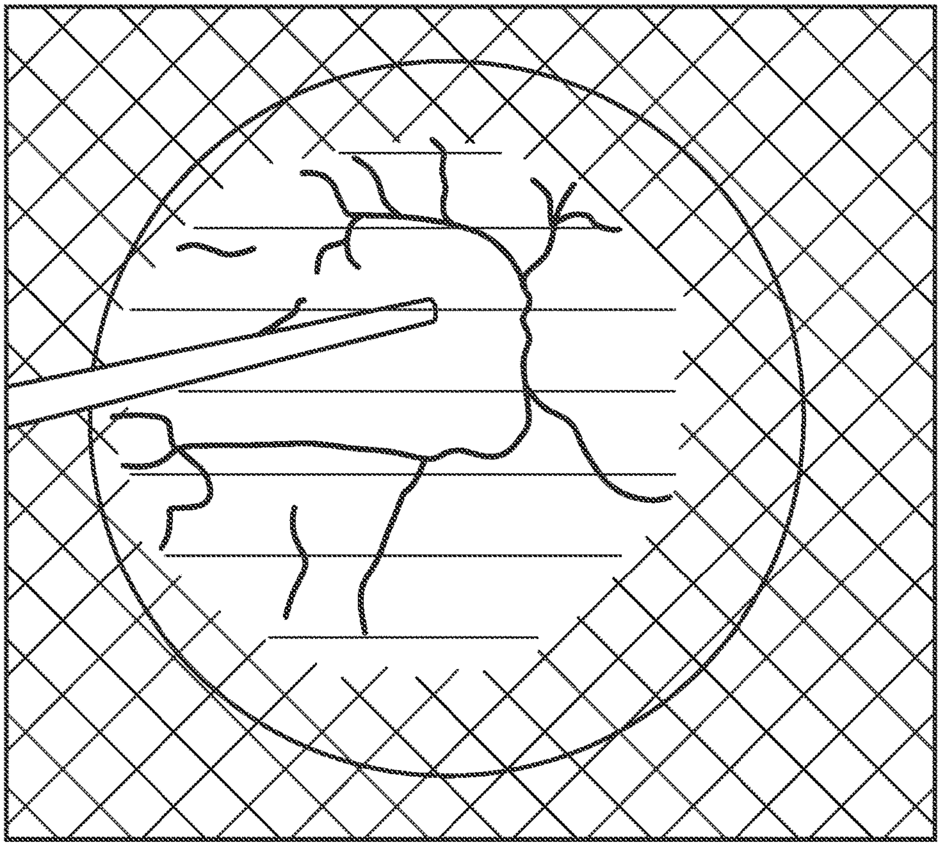
FIG. 7 shows a schematic drawing illustrating a lack of illumination and resulting poor visibility of a surgical site in deep cavities.

FIG. 6 shows schematic drawings of examples of different types of light beams generated by endo-illuminators, ranging from a narrow and symmetrical beam 610, a slightly wider symmetrical beam 620, a wide symmetrical beam 630 and an asymmetrical beam 640. In FIG. 7, a schematic drawing is provided, illustrating a lack of illumination, and resulting poor visibility of the surgical site in deep cavities.

In the proposed concept, camera settings are dynamically updated from real-time data from surgical illumination systems (e.g., retinal endo-illumination systems) which allows for a more consistent homogenously illuminated surgical view, independent of changes in illumination intensity or in color wavelength spectrum. This allows surgeons to perceive a uniform depth of field, resolution, illumination, and texture of the surgical site of interest, even when adjustments or movements to the source of lighting is performed during surgery. Thus, for surgeons (and other practitioners), the proposed concept may provide ability to perceive a uniform depth of field, resolution, illumination, and texture of the surgical site of interest, independent of adjustments or movements performed during surgery.

The proposed concept relates to an approach for providing an automatic calibration of the surgical image based on inputs from an illumination system. Camera settings (such as exposure, color balance, contrast, shadows, highlights, brightness, saturation, vibrancy, sharpness, etc.) are dynamically adjusted based on real-time data from a surgical illumination system (e.g., one or more retinal endo-illumination systems). Data from the illumination system(s) is provided over a wired, wireless or network connection to the imaging system.

This data may include illumination parameters, such as one or more lux intensity values, one or more color wavelength spectrums and an angular aperture of the illumination. For example, the connection may be based on ISO/IEEE 11073 SDC, which is a family of international standards for interoperable exchange of real-time information between medical devices and external systems in dynamic IP networks. TLS (Transport Layer Security) 1.2+ may be applied to encrypt the communication, and each device may trust the connection based on the respective certificate authorization and authentication.

The imaging system receives said illumination data, then processes and interprets a set of improved or optimally calibrated adjustments in settings (such as one or more of exposure, color balance, contrast, shadows, highlights, brightness, saturation, vibrancy, sharpness, etc.) to allow for a quick reaction to the current changes of the illumination system. For example, spectral data from multiple calibration points can be collected along the color setting axis of the illumination system. During operation, the camera may interpolate between these calibration points and set the color correction matrix as well as white balance gains to improve color rendering. In addition, machine learning algorithms can be incorporated to allow for smarter automatic adjustments if a feedback loop can be established.

As is evident from FIGS. 3 to 5, the tip of an endoilluminator probe can move around the eye chamber (unless it is a chandelier probe). This causes the distance to vary between the probe and retina. Because the light coming from the probe has the shape of a cone, the lit area also changes its size and brightness as the probe is moved. Typically, auto-exposure of the camera image operates based on the light intensity distribution among the camera pixels. When the light probe is close to the retina, the pixels observing the lit area become saturated, and no reliable intensity measurement may be available. Meanwhile, the rest of the scene may be unlit and dark and may cause the auto-exposure process to further increase the gain or exposure duration to brighten it. With the proposed concept, in which the light intensity of the endoilluminator is communicated to the microscope camera, the camera can limit its range of auto-exposure settings to those likely appropriate with the light source setting and avoid overexposing the scene.

Moreover, a scientific or surgical imaging system, such as a surgical microscope can be used with different light sources at different times. In addition, some endo-illuminators offer adjustable color balance through filters or tunable light sources to allow trade-offs between color reproduction and phototoxicity. With such variability in color balance, automatic white balance is usually enabled on microscope cameras to avoid excessive color cast in the captured video. Because the retina is generally yellow-orange in color and has no neutral-colored area, auto white balance cannot easily separate the effect of the light source from the reflectance of the scene. This may cause inaccurate color balance in the video, where the natural color of the retina is suppressed. Using the proposed concept, the light source's color balance may be transmitted to the camera. The camera can then constrain its auto white balance search to a set of plausible options given the light and produce a video output better resembling the binocular view.

These adjustments allow for a higher consistency and a more homogenously illuminated surgical view, even when changes in lux intensity or color wavelength spectrum are applied. By reacting dynamically to the changes in illumination, the camera system can provide a consistent homogenous exposure to the surgical site of interest while reducing noise levels, e.g., to a minimum. In addition, the natural colors of the surrounding tissues or the enhancements made through staining can be preserved even through adjustments in wavelengths. This allows for a brighter, sharper, and color-balanced surgical view throughout the workflow.

In other systems, "camera scene files" are used to set the settings of the camera. Camera scene files are calibrated settings that are fixed (i.e., that do not change during surgery). In the proposed concept, in addition to the scene files (which may be kept for legacy purposes), or instead of the scene files, the settings may be adjusted dynamically. FIG. 8 shows a schematic diagram of a user interface allowing a user to select a scene file or a dynamic scene file (i.e., a dynamic adjustment of the camera settings). On the top, FIG. 8 shows various tabs, such as Main, Speed/Tilt, Footswitch and, in the foreground, Camera Settings 810. Inside the camera settings, scene files ("XXX") 1 through 10. In addition, dynamic scene files YYY 1 and YYY2 are shown. The dynamic Scene Files YYY 1 and YYY 2 are offered on the user interface as an additional option, e.g., (only) when illumination systems are connection with microscope.

Figure 9:
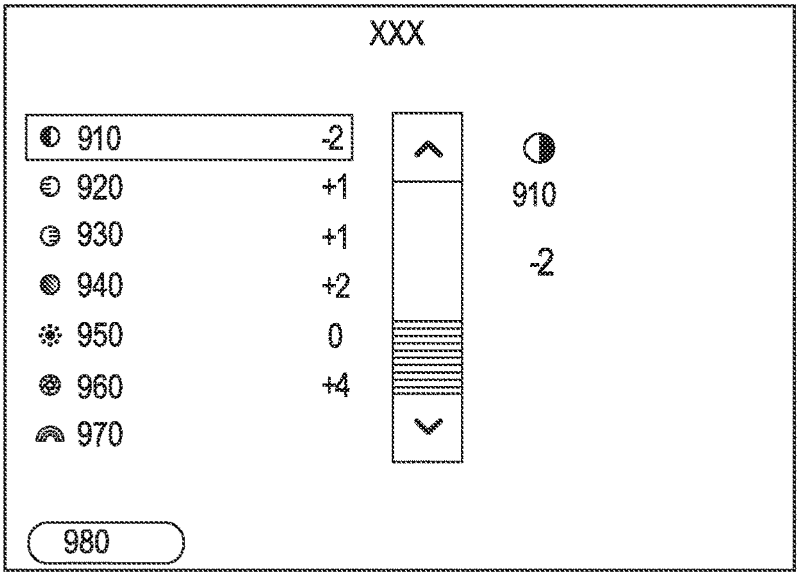
FIG. 9 shows an example of settings contained in a scene file.

FIG. 9 shows an example of the settings contained in a scene file. In the example of FIG. 9, these settings include Contrast (910), Shadows (920), Highlights (930), Saturation (940), Brightness (950), Aperture (960) and Color Balance (970). In addition, the user has the option to select a preset (980). One or more of these settings may be dynamically determined by the proposed concept. For example, the imaging system may receive the illumination data (i.e., the information on the one or more illumination parameters of the illumination system) from the illumination system(s), and then process and interpret a set of improved or optimally calibrated adjustments in the camera settings (such as exposure, color balance, contrast, shadows, highlights, brightness, saturation, vibrancy, sharpness, etc.) to allow for a quick reaction to the current changes of the illumination system. As a result, consistent and homogeneous exposure and color may be applied to the surgical site, independent of adjustments to illumination lux intensity or color wavelength spectrum during surgery.

FIGS. 10*a* to 10*f* show an example of a determination of an exposure (duration) parameter of the camera (optional imaging sensor). A set of likelihood functions can be constructed using training samples or by modelling the light reflection and transmission of typical posterior surgeries. There can be multiple such functions, each for a particular light intensity, or a group of otherwise identical functions shifted by the amount of exposure difference between them. This light intensity parameter can be a single number from the light source (input intensity), or a set of parameters including light intensity and the light probe used (a function of the output intensity). In FIGS. 10*a*, 10*b*, 10*c*, 10*e*, the x-axis shows an exposure setting, and the y-axis the likelihood of the respective exposure setting being correct. In FIG. 10*a*, a light-intensity based likelihood function 1010 is shown for a light intensity B, along with a current exposure setting 1020. The relationship between light-intensity based likelihood function 1010 and the current setting 1020 suggests that over-exposure is likely. in FIG. 10*b*, the light-intensity based likelihood functions 1030, 1010 and 1040 are shown for a light intensities A, B and C, respectively. In FIG. 10*c*, a histogram-based likelihood function 1050 is shown, that is derived from the input histogram shown in FIG. 10*d*. The histogram of FIG. 10*d* alone is inclusive. It suggests either under-exposure of most of the scene (see portion 1060 of the histogram) or over-exposure of a small spotlight (portion 1070 of the histogram). Given a live scene, the imaging system combines the endo-illuminator's intensity parameter and its own histogram to determine whether the intention of the user is more likely to shine light on a large area or a small spot. In FIG. 10*e*, the light-intensity based likelihood function 1010 (of light intensity B actually being used) and the histogram-based likelihood function 1050 are combined, showing that the new setting 1080 is to be part of the intersection of the left peak of histogram-based likelihood function 1050 and the light-intensity based likelihood function 1010, as the right peak does not meaningfully intersect with light-intensity based likelihood function 1010. The result is shown in FIG. 10*f*-combining these two pieces of information makes the decision clear: reduce exposure setting to correct the over-exposure in the spotlight area (see portion 1090 of the resulting histogram shown in FIG. 10*f*). In the case of spotlight illumination, the auto-exposure algorithm can safely ignore the darker areas of the scene and focus on bringing the highlight into optimal exposure. Note that the exposure decision still depends on the histogram (or other intensity distribution) measurements, as a fixed relationship between light intensity and exposure setting does not account for the variations in probe distance, transmittance, or reflectance. This process can be seen as increasing maximizing the likelihood of the exposure setting based on both histogram and light intensity information. Machine learning algorithms can be trained using real or simulated posterior surgical sessions with recorded camera histograms and light intensity settings as inputs, and some manual exposure set by the user as targets.

Auto white balance can similarly benefit from external light source's color parameters as constraints. With the retina exhibiting its natural yellow-orange color and the application of white, blue, or green dyes, the auto white balance algorithm cannot reliably distinguish scene reflectance and transmittance from the incident light color. This is further complicated if the white balance target is to mimic human observers' adaptation to different light colors. FIGS. 11*a* and 11*b* show an example of dynamically determining a color balance. FIG. 11*a* shows a CIE 1931 chromaticity diagram with plotted black body locus and correlated color temperatures. In FIG. 11*b*, an illustration is shown of how the search area for the color balance can be restricted based on the illumination data. Small circles 1110 represent the chromaticity spread of various light sources, or a light source at different color settings. The bigger ovals 1120 represent the white balance search area. Using the proposed concept, the light source can send its chromaticity coordinates or similar color balance information to the microscope camera. The camera then limits its auto white balance search to some area in the vicinity of these coordinates, with variable spread and likelihood values along different directions.

The likelihood functions or constraints in some other forms, may come from measurements of real or simulated surgical scenes, and target subjectively realistic color rendering if the intention is to emulate optical binocular views on screen.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to a microscope comprising a system as described in connection with one or more of the FIGS. 1*a* to 11*b*. Alternatively, a scientific or surgical imaging system, such as a microscope may be part of or connected to a system as described in connection with one or more of the FIGS. 1*a* to 11*b*. FIG. 12 shows a schematic illustration of a system 1200 configured to perform a method described herein. The system 1200 comprises a scientific or surgical imaging system (e.g., a microscope) 1210 and a computer system 1220. The scientific or surgical imaging system 1210 is configured to take images and is connected to the computer system 1220. The computer system 1220 is configured to execute at least a part of a method described herein. The computer system 1220 may be configured to execute a machine learning algorithm. The computer system 1220 and microscope 1210 may be separate entities but can also be integrated together in one common housing. The computer system 1220 may be part of a central processing system of the microscope 1210 and/or the computer system 1220 may be part of a subcomponent of the microscope 1210, such as a sensor, an actor, a camera or an illumination unit, etc. of the microscope 1210.

The computer system 1220 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 1220 may comprise any circuit or combination of circuits. In one embodiment, the computer system 1220 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 1220 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 1220 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 1220 may also include a display device, one or more speakers, and a keyboard and/or controller, which can include a mouse, trackball, touch screen, voice-recognition device, or any other device that permits a system user to input information into and receive information from the computer system 1220.

Some or all of the method steps may be executed by (or using) a hardware apparatus, like for example, a processor, a microprocessor, a programmable computer, or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine-readable carrier.

Other embodiments comprise the computer program for performing one of the methods described herein, stored on a machine-readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device, or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Embodiments may be based on using a machine-learning model or machine-learning algorithm.

Some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a pre-processing step before performing classification or predictions. Feature learning may be based on principal components analysis or cluster analysis, for example.

In some examples, anomaly detection (i.e., outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g., a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g., be used to store, manipulate, or apply the knowledge.

Machine-learning algorithms are usually based on a machine-learning model. In other words, the term "machine-learning algorithm" may denote a set of instructions that may be used to create, train, or use a machine-learning model. The term "machine-learning model" may denote a data structure and/or set of rules that represents the learned knowledge (e.g., based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g., of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e., to achieve a desired output for a given input. For example, the machine-learning model may be a deep neural network, e.g., an artificial neural network with one or more hidden layers (i.e., layers comprising only hidden nodes).

Alternatively, the machine-learning model may be a support vector machine, a random forest model or a gradient boosting model. Support vector machines (i.e., support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

LIST OF REFERENCE NUMERALS

50 Illumination system, endo-illuminator
100 Scientific or surgical imaging system
110 System
112 Interface
114 Processor
116 Storage device
120 Scientific or surgical imaging device
130*a-c* Displays
210 Obtaining information on one or more illumination parameters
220 Determining at least one parameter for using an optical imaging sensor
300 Eye
310 Endo-illuminator
320 Vitreous cutter
410 Endo-illuminator
415 Connection to Xenon light source
420 Rigid optical fiber
425 Connection to Xenon light source
430 Sclera
440 Choroid
450 Retina
510 Light source
520 Vitrector
530 Light beam
540 Retina
550 Bleeding
610-640 Light beams
810 Camera settings tab
910 Contrast setting
920 Shadows setting
930 Highlights setting
940 Saturation setting
950 Brightness setting
960 Aperture setting
970 Color balance setting
980 Preset
1010, 1030, 1040 Likelihood functions of different illumination settings
1020 Current exposure setting
1050 Likelihood function according to histogram
1060 Left portion of histogram
1070 Right portion of histogram
1080 New exposure setting
1090 Portion of histogram
1110 Small circles representing chromaticity spread of light sources/settings
1120 White balance search area
1200 System
1210 Imaging device
1220 Computer system

The invention claimed is:

1. A system for a scientific or surgical optical imaging system, the system comprising one or more processors and one or more storage devices, wherein the system is configured to:

obtain information on one or more illumination parameters used by an illumination system being separate from the scientific or surgical optical imaging system from the illumination system; and determine at least one parameter for using an optical imaging sensor of an imaging device of the scientific or surgical optical imaging system based on the one or more illumination parameters.

2. The system according to claim 1, wherein the system is configured to determine at least one of an image processing parameter and an image acquisition parameter based on the one or more illumination parameters.

3. The system according to claim 1, wherein the system is configured to determine at least one of an exposure duration parameter, a sensitivity parameter, an aperture parameter, a brightness parameter, a shadow recovery parameter, a highlight recovery parameter, and at least one white balance parameter based on the one or more illumination parameters.

4. The system according to claim 1, wherein the one or more illumination parameters comprise at least one of an illumination intensity parameter, an illumination angle parameter, and an illumination wavelength parameter.

5. The system according to claim 1, wherein the system is configured to limit a search space for determining the at least one parameter for using the optical imaging sensor based on the one or more illumination parameters, and to determine the at least one parameter based on the limited search space.

6. The system according to claim 5, wherein the system is configured to limit a search space for determining at least one white balance parameter for using the optical imaging sensor based on at least one of an illumination intensity parameter and an illumination wavelength parameter included in the one or more illumination parameters.

7. The system according to claim 6, wherein the system is configured to limit the search space for determining the at least one white balance parameter based on an expected composition of a sample being illuminated by the illumination system and being observed by the optical imaging sensor.

8. The system according to claim 5, wherein the system is configured to limit a search space for determining at least one of an exposure duration parameter, a sensitivity parameter, an aperture parameter, a brightness parameter, a shadow recovery parameter, and a highlight recovery parameter for using the optical imaging sensor based on at least one of an illumination intensity parameter and an illumination angle parameter included in the one or more illumination parameters.

9. The system according to claim 8, wherein the system is configured to determine at least one of the exposure duration parameter, the sensitivity parameter, the aperture parameter, the brightness parameter, the shadow recovery parameter, and the highlight recovery parameter based on the limited search space and based on a histogram of imaging sensor data of the optical imaging sensor.

10. The system according to claim 1, wherein the system is configured to determine the at least one parameter for using the optical imaging sensor based on an output of a machine-learning model being trained to determine the at least one parameter, wherein the one or more illumination parameters and at least a histogram of imaging sensor data of the optical imaging sensor are used as input to the trained machine-learning model.

11. The system according to claim 10, wherein the system is configured to adjust the machine-learning model, using supervised learning, during operation of the scientific or surgical imaging system using one or more sets of training data, each set of training data comprising the one or more illumination parameters, at least the histogram of the imaging sensor data, and at least one manually selected parameter for using the optical imaging sensor of an instance where a user has manually selected the at least one parameter.

12. The system according to claim 1, wherein the system is configured to output a display signal to a display device of the scientific or surgical imaging system, the display signal being based on the at least one parameter for using the optical imaging sensor and based on imaging sensor data of the optical imaging sensor.

13. The system according to claim 1, wherein the system is a system for an ophthalmic microscope, and wherein the system is configured to obtain the information on the one or more illumination parameters from an ophthalmic endo-illumination system.

14. A method for a scientific or surgical optical imaging system, the method comprising:

obtaining, by the scientific or surgical optical imaging system, information on one or more illumination parameters used by an illumination system being separate from the scientific or surgical optical imaging system from the illumination system; and determining at least one parameter for using an optical imaging sensor of an imaging device of the scientific or surgical optical imaging system based on the one or more illumination parameters.

15. A non-transitory machine-readable storage medium including a program code configured to perform, when executed by a processor, the method according to claim 14.

* * * * *